(12) United States Patent
Hu et al.

(10) Patent No.: US 6,652,845 B2
(45) Date of Patent: Nov. 25, 2003

(54) LAYER MATERIALS TREATED WITH DURABLE ACIDIC ODOR CONTROL/ BINDER SYSTEMS

(75) Inventors: Sheng-Hsin Hu, Appleton, WI (US); Tong Sun, Neenah, WI (US); Ronald L. Edens, Cumming, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 10/025,215

(22) Filed: Dec. 18, 2001

(65) Prior Publication Data

US 2003/0113289 A1 Jun. 19, 2003

(51) Int. Cl.[7] .............................. A61L 9/00; A61L 9/01; A61L 9/014; A01N 25/34
(52) U.S. Cl. ...................... 424/76.1; 424/400; 424/402; 424/404
(58) Field of Search ................................ 424/76.1, 400, 424/402, 404

(56) References Cited

U.S. PATENT DOCUMENTS

| | | | |
|---|---|---|---|
| 3,707,148 A | 12/1972 | Bryce | 128/284 |
| 3,794,034 A | 2/1974 | Jones, Sr. | 128/290 |
| 4,385,632 A | 5/1983 | Odelhög | 604/360 |
| 4,479,795 A | 10/1984 | Mustacich et al. | 604/53 |
| 5,874,164 A * | 2/1999 | Caldwell | 428/306.6 |

FOREIGN PATENT DOCUMENTS

| | | | | |
|---|---|---|---|---|
| EP | 311 344 | | 4/1989 | ........... A61L/15/00 |
| EP | 392 528 | | 10/1990 | ........... A61L/15/46 |
| JP | 1-104885 A | * | 4/1989 | ........ D06M/15/564 |
| WO | 99/32697 | | 7/1999 | .......... D06M/15/03 |
| WO | 99/45976 | | 9/1999 | ........... A61L/15/46 |
| WO | WO 99/61518 | * | 12/1999 | .............. C08J/9/00 |
| WO | 00/50098 | | 8/2000 | ........... A61L/15/48 |
| WO | 01/32226 | | 5/2001 | ........... A61L/15/20 |

\* cited by examiner

Primary Examiner—Thurman K. Page
Assistant Examiner—Simon J. Oh
(74) Attorney, Agent, or Firm—Pauley Petersen & Erickson

(57) ABSTRACT

A thermoplastic layer material has at least one odor reducing surface which is treated with a carboxylic acid-based odor control agent, and which is able to withstand insults with an aqueous liquid. The acid-based odor control agent is bound to the layer material by an organosilicone polymer binder. The binder is water-insoluble, and can form a highly gas-permeable coating. The binder is also highly porous, so as to expose the odor control agent to ammonia and other odoriferous gases which it is intended to control.

47 Claims, No Drawings ically acid compound for inhibiting the formation of ammonia from urea in urine. Odor absorbers and adsorbers remove odor after it is formed. Examples of odor control agents that remove odor by absorption or adsorption include activated carbon, silica, and cyclodextrin.
LAYER MATERIALS TREATED WITH DURABLE ACIDIC ODOR CONTROL/ BINDER SYSTEMS

FIELD OF THE INVENTION

The present invention is directed to layer materials such as nonwoven webs, films, and the like, which are treated with acidic odor control compounds that are not easily washed away.

BACKGROUND OF THE INVENTION

Nonwoven fabrics, films, foams, and other layer materials and their manufacture have been the subject of extensive development resulting in a wide variety of materials for numerous applications. For example, nonwovens of light basis weight and open structure are used in personal care items such as disposable diapers as liner fabrics that provide dry skin contact but readily transmit fluids to more absorbent materials which may also be nonwovens of a different composition and/or structure. Nonwovens of heavier weights may be designed with pore structures making them suitable for filtration, absorbent and barrier applications such as wrappers for items to be sterilized, wipers or protective garments for medical, veterinary or industrial uses. Even heavier weight nonwovens have been developed for recreational, agricultural and construction uses. Films, foams, and other layer materials are also employed in some of these applications, and may be combined with nonwoven webs.

For many thermoplastic layer material end use applications, it is desirable to reduce, prevent, or eliminate odors. For diapers and other incontinence products, it is desirable to reduce or eliminate the odor of ammonia which is present in urine. For feminine hygiene products, it is desirable to reduce or eliminate the odors of trimethylamine and triethylamine. Other common odor-producing substances include isovaleric acid, dimethyl disulfide, and dimethyl trisulfide.

Odor control agents include odor inhibitors, odor absorbers, odor adsorbers and other compounds which reduce, prevent, or eliminate odors. Odor inhibitors prevent the odor from forming. For example, U.S. Pat. No. 4,273,786 to Kraskin teaches the use of an aminopolycarboxylic acid compound for inhibiting the formation of ammonia from urea in urine. Odor absorbers and adsorbers remove odor after it is formed. Examples of odor control agents that remove odor by absorption or adsorption include activated carbon, silica, and cyclodextrin.

Acidic odor control agents based on carboxylic acids and their derivatives are used to neutralize or inhibit formation of odors from ammonia and other basic odor-forming compounds. Ammonia, released from aqueous ammonium hydroxide, is one of the primary odor-producing substances in urine. One of the drawbacks of acidic odor control agents is they are not inherently durable, i.e., they do not perform well after multiple insults with aqueous liquids. To the contrary, aqueous odor control agents are typically water-soluble, and can be easily washed away.

Water-insoluble, film-forming polymers can be used as a coating or binder applied to the layer material, to protect the acidic odor control agents from dissolution and washing. However, these polymers may also inhibit the performance of the odor control agents by preventing the ammonia from ever reaching them.

There is a need or desire for layer materials treated with acidic odor control agents which have durable odor control properties over multiple insults with an aqueous liquid. Specifically, there is a need or desire for a binder between carboxylic acid odor control agents and the layer materials which prevents or reduces the washing away of the odor control agents without significantly preventing or reducing their odor control performance.

DEFINITIONS

The term "layer material" refers to a material that exists in the form of a flexible, fabric-like or paper-like material, including without limitation nonwoven filament webs and fabrics, thermoplastic films, flexible thermoplastic foam materials, and multilayer combinations including one or more of these.

The term "water-permeable porous layer material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

The term "nonwoven fabric or web" means a web having a structure of individual fibers or threads which are interlaid, but not in a regular or identifiable manner as in a knitted fabric. Nonwoven fabrics or webs have been formed from many processes such as, for example, meltblowing processes, spunbonding processes, air laying processes, and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, microfibers may have an average diameter of from about 1 micron to about 30 microns. Another frequently used expression of fiber size is denier, which is defined as grams per 9000 meters of a fiber. For a fiber having circular cross-section, denier may be calculated as fiber diameter in microns squared, multiplied by the density in grams/cc, multiplied by 0.00707. A lower denier indicates a finer fiber and a higher denier indicates a thicker or heavier fiber. For example, the diameter of a polypropylene fiber given as 15 microns may be converted to denier by squaring, multiplying the result by 0.89 g/cc and multiplying by 0.00707. Thus, a 15 micron polypropylene fiber has a denier of about 1.42 ($15^2 \times 0.89 \times 0.00707 = 1.415$). Outside the United States the unit of measurement is more commonly the "tex," which is defined as the grams per kilometer of fiber. Tex may be calculated as denier/9.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average diameters larger than about 7 microns, more particularly, between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the present invention are preferably substantially continuous in length.

The term "film" refers to a thermoplastic film made using a film extrusion process, such as a cast film or blown film extrusion process. The term "water-permeable porous films" refers to films rendered porous by puncturing or aperturing, and to films rendered porous by mixing polymer with filler, forming a film from the mixture, and stretching the film.

The term "foam material" refers to a thermoplastic layer material made with the aid of a foaming process. The term "open-celled foam material" refers to a foam layer whose cells interconnect, or otherwise create pores from one surface of the layer to the opposite surface.

The term "polymer" includes, but is not limited to, homopolymers, copolymers, such as for example, block, graft, random and alternating copolymers, terpolymers, etc., and blends and modifications thereof. Furthermore, unless otherwise specifically limited, the term "polymer" shall include all possible geometrical configurations of the material. These configurations include, but are not limited to isotactic, syndiotactic and atactic symmetries.

The term "carboxylic acid-based odor control agent" includes odor control agents based on carboxylic acids and/or their partially neutralized salts. The term "multi-carboxylic acid-based odor control agent" includes odor control agents based on dicarboxylic acids, tricarboxylic acids, polycarboxylic acids, polymeric polycarboxylic acids, etc., and/or their partially neutralized salts.

The term "polymeric polycarboxylic acid" refers to a polymer having multiple carboxylic acid groups in its repeating units. Examples include polyacrylic acid polymers, polymaleic acid polymers, copolymers of acrylic acid, copolymers of maleic acid, and combinations thereof. Other examples are disclosed in U.S. Pat. No. 5,998,511, which is incorporated by reference.

The terms "silicone polymer," "polyorganosiloxane" and "polysiloxane" interchangeably refer to siloxane polymers based on a structure of alternating silicon and oxygen atoms with various organic radicals attached to the silicon:

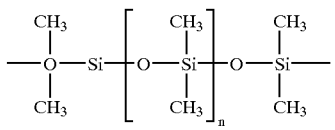

The term "odor control system" refers collectively to individual odor control agents, and combinations (by chemical reaction and/or blending) of two or more odor control agents.

SUMMARY OF THE INVENTION

The present invention is directed to layer materials treated with a combination of odor control system and binder, where the odor control system includes a carboxylic acid odor control agent and the binder includes a polyorganosiloxane (i.e., silicone polymer). The inventors have found that silicone polymers serve as excellent binders between carboxylic odor control agents (and systems containing them) and thermoplastic layer materials, particularly layer materials based on polypropylene, polyethylene and other polyolefins. The silicone polymers have a unique ability to protect the acidic odor control agents from being dissolved or washed away by aqueous liquids, while at the same time permitting odoriferous gases such as ammonia to reach the odor control agents. Put another way, the silicone polymers are water insoluble, and at the same time are highly porous.

In one embodiment of the invention, the odor control system and silicone polymer are combined together, with the silicone polymer being in a molten form or dissolved or suspended in a solvent. The combination of odor control system and silicone polymer are applied to the layer material by spray coating, brushing, printing, dipping, extrusion, or the like.

In another embodiment of the invention, the odor control system is first applied to the layer material using spray coating, brushing, printing, dipping, extrusion, or the like. The silicone polymer is then applied to the layer material over the odor control agent using spray coating, brushing, printing, dipping, extrusion, or the like.

In one embodiment of the invention, the odor control system includes a multi-carboxylic acid-modified chitin or chitosan complex odor control agent. The carboxyl sites facilitate absorption of ammonia and amine-based odors. The amino groups on the chitin or chitosan facilitate absorption of acid-based odor compounds, and suppress the enzymatic decomposition of urine and menses, thereby inhibiting odor generation. This odor control complex can also be combined with activated carbon to provide additional control of amino, sulfuric and acidic odors.

DETAILED DESCRIPTION OF THE PRESENTLY PREFERRED EMBODIMENTS

In accordance with the invention, an odor control system including an acidic odor control agent is used in conjunction with a silicone polymer binder to provide a layer material with the ability to control odors from aqueous ammonia and other basic odoriferous compounds, and to maintain the ability to control odor after one or more aqueous liquid insults.

The layer material can be a thermoplastic material, made using one or more thermoplastic polymers. The layer material may be porous and water-permeable. The layer material may be a thermoplastic nonwoven filament web, a thermoplastic film, a foam layer, or a combination thereof. A thermoplastic nonwoven filament web is preferred. The treated thermoplastic layer material can be used in a wide variety of personal care products and medical products, and in other applications.

A wide variety of thermoplastic polymers may be used to construct the thermoplastic layer material, including without limitation polyamides, polyesters, polyolefins, copolymers of ethylene and propylene, copolymers of ethylene or propylene with a $C_4$–$C_{20}$ alpha-olefin, terpolymers of ethylene with propylene and a $C_4$–$C_{20}$ alpha-olefin, ethylene vinyl acetate copolymers, propylene vinyl acetate copolymers, styrene-poly(ethylene-alpha-olefin) elastomers, polyurethanes, A–B block copolymers where A is formed of poly(vinyl arene) moieties such as polystyrene and B is an elastomeric midblock such as a conjugated diene or lower alkene, polyethers, polyether esters, polyacrylates, ethylene alkyl acrylates, polyisobutylene, poly-1-butene, copolymers of poly-1-butene including ethylene-1-butene copolymers, polybutadiene, isobutylene-isoprene copolymers, and combinations of any of the foregoing. Polyolefins are desirable. Polyethylene and polypropylene homopolymers and copolymers are most desirable.

The desired layer material for the invention is a nonwoven web including a plurality of filaments made from one or more polymers. The nonwoven web may be a spunbond web, a meltblown web, a bonded carded web, or another type of nonwoven web, and may be present in a single layer or a multilayer composite including one or more nonwoven web layers and, in some instances, one or more film or foam layers. The web may include monocomponent or bicomponent filaments, or a combination including one or both filament types. The nonwoven web may have a variety of basis weights, preferably ranging from about 0.1-200 grams per square meter (gsm).

The odor control system includes at least one acidic odor control agent, desirably a carboxylic acid-based odor control agent. Suitable carboxylic acid odor control agents include without limitation hydroxycarboxylic acids such as citric acid, malic acid, tartaric acid, and the like. Other suitable carboxylic acid odor control agents include without limitation formic acid, acetic acid, propionic acid, butyric acid, isobutyric acid, pyruvic acid, glycolic acid, lactic acid, and combinations thereof.

The acidic odor control agent may be combined (i.e., mixed or reacted) with one or more compatible odor-control agents to provide enhanced odor control properties. For instance a hydroxy carboxylic odor control agent, or another multi-carboxylic acid odor control agent, may be combined with chitin or chitosan. This can be accomplished by blending a calculated amount of chitin and/or chitosan with a calculated amount of an aqueous solution of the multi-carboxylic acid odor control agent at room temperature for 30 minutes, and then drying the mixture in an oven at 50° C. for eight hours. The acid concentration in the starting aqueous solution is desirably in the range of about 5–55% by weight. The degree of diacetylation in the chitosan should be determined before adding chitosan to the acid solution. The amount of chitosan added to the acid solution should be selected so that the molar equivalent ratio of free amino groups in the chitosan to free carboxyl groups in the multi-carboxylic acid is about 0.2–0.4. The resulting odor control system is useful in absorbing, neutralizing, and inhibiting formation of ammonia, trimethylamine, isovaleric acid, and similar odoriferous compounds. In this embodiment, the acid is suitably citric acid, malic acid or tartaric acid, and is desirably citric acid.

A multi-carboxylic acid odor control agent may also be combined with a metal-oxide, suitably zinc oxide, to adjust the pH of the odor control agent by partially converting the free acid groups to their metallic salts. Other suitable metal oxides include transition metals such as cadmium, zirconium, chromium, copper, and the like. This partial neutralization of the multi-carboxylic acids can render them more useful for treating layer materials which contact the human body. The resulting odor control system is useful in absorbing, neutralizing, and inhibiting formation of ammonia, trimethylamine, isovaleric acid, and similar odoriferous compounds. In this embodiment, the acid is suitably citric acid, malic acid or tartaric acid, and is desirably citric acid.

The acidic odor control agent may also be a chelating agent. Suitable chelating agents include without limitation aminopolycarboxylic acids, their alkali metal salts, and combinations thereof. Suitable aminopolycarboxylic acids and alkali metal (preferably sodium) salts thereof, include without limitation ethylenediamine tetraacetic acid (EDTA), the alkali metal salts of EDTA (for instance, $Na_2$ EDTA, $Na_3$ EDTA, and $Na_4$ EDTA), nitrilotriacetic acid, the alkali metal (e.g., sodium) salts of cyclohexanediamine tetraacetic acid, diethylenetriamine pentaacetic acid (DTPA), hydroxyethyl-enediamine triacetic acid (HEDTA), pentasodium diethyl-enetriamine pentaacetate, trisodium hydroxyethyl ethylene-diamine triacetate, and combinations thereof. A particularly suitable aminopolycarboxylic acid is EDTA. Suitable chelating agents also include polyamino disuccinic acids and alkali metal salts of them, including acids and salts of ethylenediamine-N,N'-disuccinic acid, diethylenetriamine-N,N"-disuccinic acid, triethylenetetraamine-N,N'"-disuccinic acid, 1,6-hexamethylenediamine N,N-disuccinic acid, tetraethylenepentaamine-N,N""-disuccinic acid, 2-hydroxypropylene-1,3-diamine-N,N'-disuccinic acid, 1,2-propylenediamine-N,N'-disuccinic acid, 1,3-propylenediamine-N,N'-disuccinic acid, cis-cyclohexanediamine-N,N'-disuccinic acid, trans-cyclohexanediamine-N,N'-disuccinic acid, and ethylene-bis (oxyethylenenitrilo)-N,N'-disuccinic acid. One suitable polyamino disuccinic acid is ethylenediamine-N,N'-disuccinic acid. Chelating agents can act as odor inhibitors which prevent odor from occurring by interfering with reactions that produce odors, as well as odor absorbents which remove or minimize existing odor-producing compounds.

In another embodiment of the invention, activated carbon can also be added to the odor control system. Activated carbon helps to prevent or reduce various odors such as triethylamine, trimethylamine, dimethyl disulfide, and isovaleric acid, but does not alone neutralize ammonia odor. By combining activated carbon particles or fibers with the multicarboxylic-acid based odor control agents and combinations described above, an order control system can be devised which prevents and/or reduces a wide variety of odors. In this embodiment, the silicone polymer binder described below serves dual purposes of a) binding the acid-based odor control agents and combinations described above to the thermoplastic layer material, and b) binding the activated carbon to the acid-based odor control agents and combinations, and/or to the thermoplastic layer material.

The binder includes a polyorganosiloxane (i.e., a silicone polymer). As described above, a silicone polymer contains a repeating silicon-oxygen backbone and has organic groups "R" attached to a significant portion of the silicon atoms by silicon-carbon bonds. Suitable "R" groups include, without limitation, methyl, longer alkyl, fluoroalkyl, phenyl, vinyl and the like. Specific silicone polymers include, without limitation, poly(hexamethyldisiloxane), poly(octamethyltrisiloxane), poly(decamethyltetrasiloxane), poly(octamethylcyclotetrasiloxane), poly(octaphenylcyclotetrasiloxane), and combinations thereof. Silicone polymers may be in the form of homopolymers, random copolymers, block copolymers, and combinations thereof. Preferred silicone polymers vary with the method of application to the layer material. Silicone polymers having higher melting points (above room temperature but below the melting point of the layer material substrate) are more suitable for extrusion. Silicone polymers having lower melting points (which exist as grease or liquid at room temperature) are more suitable for application by spraying, dipping, and the like.

The amount of silicone polymer binder should be sufficient to effectively bind the odor control system to the layer material, but not so high as to unnecessarily inhibit the odor control performance. Generally, the silicone polymer should be present in an amount of about 5 to 200 parts by weight silicone polymer per 100 parts by weight of dry, water-free, solvent-free odor control system. Suitably, the silicone polymer should be present in an amount of about 10 to 100 parts by weight silicone polymer per 100 parts by weight dry odor control system, desirably in an amount of about 15 to 50 parts by weight silicone polymer per 100 parts by weight of dry odor control system. Exemplary silicone polymers which are particularly suitable as binding agents include Dow Corning® 84 Additive, Dow Corning® 36 emulsion, and Dow Corning® Q2-3195.

The silicone polymer can be combined with the odor control system before the combination is applied to the layer material substrate. A wide variety of blending techniques can be used to combine the ingredients, including without limitation melt blending, solution mixing, spray drying, fluidized bed coating, and the like. By way of example, an odor control agent including citric acid can be dissolved in water, suitably at a concentration of about 0.1–15% by weight citric acid. A calculated amount of zinc oxide can then be stirred into the acid solution to partially neutralize the free acid groups to their metallic salts, effecting a solution pH of about 4.5. Then, silicone polymer sold as Dow Corning® 84 Additive by the Dow Corning® Corporation can be added to the citric acid/zinc oxide solution in an amount of about 0.1–0.75 parts by weight silicone polymer per part by weight dry citric acid/zinc oxide system. Then, the combined silicone polymer/odor control system can be applied to a layer material substrate, such as a polyolefin fibrous nonwoven web, using melt extrusion, printing, dipping, coating, brushing, or another suitable technique. Additionally, titanium dioxide pigment may be added, for example, at up to about 0.75 parts by weight pigment per part by weight citric acid/zinc oxide system.

Alternatively, the silicone polymer can be combined with the odor control system after, or at the same time, that the odor control system is applied to the layer material substrate. A wide variety of techniques can be used to apply both the odor control system and the silicone polymer binder to the substrate, including without limitation melt extrusion, printing, dipping, coating, brushing, and the like. By way of example, an aqueous odor control system containing a hydroxycarboxylic acid and a suitable amount of chitosan can be applied using these techniques. A layer material substrate, such as a polyolefin fibrous nonwoven web, can be used as the substrate. Simultaneously, a liquid silicone polymer sold as Dow Corning® 84 Additive by the Dow Corning Corporation can be applied to the substrate. The silicone polymer and powdered odor control system will accordingly attach to the layer material substrate, and to each other.

In one embodiment of the invention, the odor control system may also include a particulate inorganic material, such as a pigment and/or filler. Particulate materials such as titanium dioxide, clay, calcium carbonate and/or silica can be added at 0.01–5% by weight, desirably 0.1–1.0% by weight of the odor control system. In addition to providing pigment, these materials contribute to porosity of the silicone polymer binder. One suitable pigment is KEMIRA®UDR-P, available from Kemira Pigment Co. of Savannah, Ga.

The amount of odor control system needed for application to the substrate will vary depending on the type of odor control agents in the system, the amount and type of odor(s) being controlled, the amount and type of silicone polymer binder, and other factors. On a dry weight basis, the odor control system should generally constitute about 0.1–10% by weight of the thermoplastic layer material to which it is applied, suitably about 0.5–8% by weight, desirably about 2–7% by weight.

The treated thermoplastic layer materials thus formed can be used in a wide variety of absorbent product applications including, in particular, personal care absorbent products. Personal care absorbent products include diapers, training pants, swim wear, absorbent underpants, baby wipes, adult incontinence products, feminine hygiene products, and the like. In absorbent products, the treated layer material (if water permeable) can be used as a cover sheet or containment matrix for an absorbent medium capable of absorbing aqueous liquids. An absorbent medium may include, for instance, pulp fibers alone or in combination with a superabsorbent material. The treated layer material can also be used in medical absorbent products, including without limitation garments, underpads, absorbent drapes, bandages, and medical wipes. Other uses include air filters, water filters, industrial wipes, poultry pads and bed pads.

While the embodiments of the invention described herein are presently preferred, various modifications and improvements can be made without departing from the spirit and scope of the invention. The scope of the invention is indicated by the appended claims, and all changes that fall within the meaning and range of equivalents are intended to be embraced therein.

We claim:

1. A treated thermoplastic layer material comprising:
   a thermoplastic substrate layer;
   an odor control system on the substrate layer, comprising a carboxylic acid-based odor control agent selected from the group consisting of multi-carboxylic acids, polymeric polycarboxylic acids, hydroxycarboxylic acids, chelating agents and combinations thereof; and
   a binder on the substrate layer, comprising an organosilicone polymer selected from the group consisting of poly(hexamethyldisiloxane), poly(octamethyltrisiloxane), poly(decamethyltetrasiloxane), poly(octamethylcyclotetrasiloxane), poly(octaphenylcyclotetrasiloxane), and combinations thereof.

2. The treated thermoplastic layer material of claim 1, wherein the substrate layer comprises a thermoplastic nonwoven filament web.

3. The treated thermoplastic layer material of claim 1, wherein the substrate layer comprises a thermoplastic film.

4. The treated thermoplastic layer material of claim 1, wherein the substrate layer comprises a thermoplastic foam layer.

5. The treated thermoplastic layer material of claim 1, wherein the substrate layer comprises a porous, water-permeable layer.

6. The treated thermoplastic layer material of claim 1, wherein the carboxylic acid-based odor control agent comprises a multi-carboxylic acid.

7. The treated thermoplastic layer material of claim 1 wherein the carboxylic acid-based odor control agent comprises a polymeric polycarboxylic acid.

8. The treated thermoplastic layer material of claim 1, wherein the carboxylic acid-based odor control agent comprises a hydroxycarboxylic acid selected from citric acid, malic acid, tartaric acid, and combinations thereof.

9. The treated thermoplastic layer material of claim 1, wherein the carboxylic acid-based odor control agent comprises citric acid.

10. The treated thermoplastic layer material of claim 1, wherein the odor control system further comprises an odor control agent selected from chitin, chitosan, and combinations thereof.

11. The treated thermoplastic layer material of claim 1, wherein the odor control system further comprises activated carbon.

12. The treated thermoplastic layer material of claim 10, wherein the odor control system further comprises activated carbon.

13. The treated thermoplastic layer material of claim 1, wherein the odor control system further comprises a metal oxide.

14. The treated thermoplastic layer material of claim 1, wherein the odor control system further comprises an inorganic particulate material.

15. The thermoplastic layer material of claim 1, wherein the binder comprises a silicone polymer selected from the group consisting of liquid silicone polymers and silicone polymer emulsions.

16. A treated thermoplastic layer material, comprising:
a thermoplastic substrate layer;
about 0.1–10%, based on the weight of the treated layer material, of an odor control system including a multi-carboxylic acid-based odor control agent; and
about 5–200 parts by weight of silicone polymer binder per 100 parts by weight of the odor control system.

17. The treated thermoplastic layer material of claim 16, comprising about 0.5–8% of the odor control system, based on the weight of the treated layer material.

18. The treated thermoplastic layer material of claim 16, comprising about 2–7% by weight of the odor control system, based on the weight of the treated layer material.

19. The treated thermoplastic layer material of claim 16, wherein the multi-carboxylic acid-based odor control agent comprises a hydroxycarboxylic acid.

20. The treated thermoplastic layer material of claim 16, wherein the multi-carboxylic acid-based odor control agent comprises a polymeric polycarboxylic acid.

21. The treated thermoplastic layer material of claim 16, wherein the multi-carboxylic acid-based odor control agent comprises citric acid.

22. The treated thermoplastic layer material of claim 16, wherein the odor control system further comprises chitin.

23. The treated thermoplastic layer material of claim 16, wherein the odor control system further comprises chitosan.

24. The treated thermoplastic layer material of claim 16, wherein the odor control system further comprises activated carbon.

25. The treated layer material of claim 16, wherein the odor control system further comprises a transition metal oxide.

26. The treated thermoplastic layer material of claim 16, comprising about 10–100 parts by weight of the silicone polymer binder per 100 parts by weight of the odor control system.

27. The treated thermoplastic layer material of claim 16, wherein the binder comprises a silicone polymer selected from liquid silicone polymers and silicone polymer emulsions.

28. The treated thermoplastic layer material of claim 16, wherein the odor control system further comprises a particulate inorganic material.

29. A treated thermoplastic layer material, comprising:
a fibrous nonwoven substrate layer;
an odor control system on the substrate layer, comprising a hydroxycarboxylic acid and chitosan; and
a binder on the substrate layer, comprising an organosilicone polymer selected from the group consisting of poly(hexamethyldisiloxane), poly(octamethyltrisiloxane), poly(decamethyltetrasiloxane). poly(octamethylcyclotetrasiloxane), poly(octaphenylcyclotetrasiloxane), and combinations thereof.

30. A diaper comprising the treated layer material of claim 29.

31. Training pants comprising the treated layer material of claim 29.

32. Swim wear comprising the treated layer material of claim 29.

33. Absorbent underpants comprising the treated layer material of claim 29.

34. A baby wipe comprising the treated layer material of claim 29.

35. An adult incontinence product comprising the treated layer material of claim 29.

36. A feminine hygiene product comprising the treated layer material of claim 29.

37. A medical garment comprising the treated layer material of claim 29.

38. An underpad comprising the treated layer material of claim 29.

39. An absorbent drape comprising the treated layer material of claim 29.

40. A bandage comprising the treated layer material of claim 29.

41. A medical wipe comprising the treated layer material of claim 29.

42. A filter comprising the treated layer material of claim 29.

43. An industrial wipe comprising treated layer material of claim 29.

44. A poultry pad comprising the treated layer material of claim 29.

45. A bed pad comprising the treated layer material of claim 29.

46. The treated thermoplastic layer material of claim 1, wherein the carboxylic acid-based odor control agent comprises a chelating agent.

47. The treated thermoplastic material of claim 16, wherein the multi-carboxylic acid-based odor control agent comprises a chelating agent.

* * * * *